Nov. 2, 1965 | E. H. SCANLON | Plant Pat. 2,566

ASH TREE

Filed June 14, 1963 | 2 Sheets-Sheet 1

INVENTOR.
EDWARD H. SCANLON
BY Ely, Gobrick & Flynn
ATTORNEYS

INVENTOR.
EDWARD H. SCANLON
BY Ely, Golrick & Flynn
ATTORNEYS

United States Patent Office

Plant Pat. 2,566
Patented Nov. 2, 1965

2,566
ASH TREE

Edward H. Scanlon, 7621 Lewis Road,
Olmsted Falls, Ohio

Filed June 14, 1963, Ser. No. 288,060
1 Claim. (Cl. Plt.—51)

This invention or discovery relates to a new and distinct ash tree variety of the species *Fraxinus oxycarpa*, characterized primarily by its brilliant wine red-colored fall foliage.

Particularly because of a strikingly beautiful coloration in the fall, this new variety presents a highly desirable ash tree both for shade and ornamental plantings. Furthermore, a rounded symmetrical head shape seems to be characteristic, which also renders this variety desirable for such planting because of its outstanding appearance at all times when in leaf. Also it has been found that in attaining the final wine red fall color, the foliage first turns from the green summer color to a beautiful purple, this change occurring throughout the tree substantially simultaneously, and thereafter develops the final coloration; the change from the purple to the final brilliant wine red color beginning at the top and spreading downward through the entire tree.

This new variety originated by discovery, among a public park planting of *Fraxinus oxycarpa* trees in Melbourne, Australia, of a tree having outstanding fall coloration hereinafter described, and a tighter, rounder, more symmetrical crown or head form than usual in the species. The characteristic fall coloration has been found to endure in propagules obtained by grafting and budding scion stock taken from the selected tree of the Australian planting onto green ash (*Fraxinus lanceolata*) understock. Thus far the tighter, rounder, more symmetrical head shape as compared with the species also appears established in the clone.

The following characteristics are observed in the propagules:

Branchlet: Color—moderate olive brown (2.5Y 4/4—Nickerson Color Fan) with numerous (35 to the inch of stem) light tan lenticels. The current year's growth is dark yellow (5Y 6/7 NCF). Shoots are glabrous; pith is white.

Leaves: Six to 10 inches long. Leaflets 9–13, color of top is moderate olive green (5GY 4/3 NCF) occasionally suffused purplish, underside moderate yellow-green (2.5GY 5/5 NCF). Leaf rachis colored deep purplish red (7.5RP 3/9 NCF) paling beneath.

Leaflets: Varying in size from 1¼″ to 2¾″ in length, width from ⅝″ to ½″ at widest part; mostly subsessile to ⅛″ stalk, mostly lanceolate but the terminal sometimes oblanceolate, base tapering and apex acuminate. A dense fringe of hairs is characteristically on one side only of the midrib at the base of the leaflet. Leaflets serrated from near the base with about 8 serrations to the inch at midleaf, the serrations blunt with incurved rounded tip. Leaflet with a narrow dark marginal band.

Winter bud: Small, dark brown, pubescent. Somewhat more compressed than appears typical.

Figure 1:
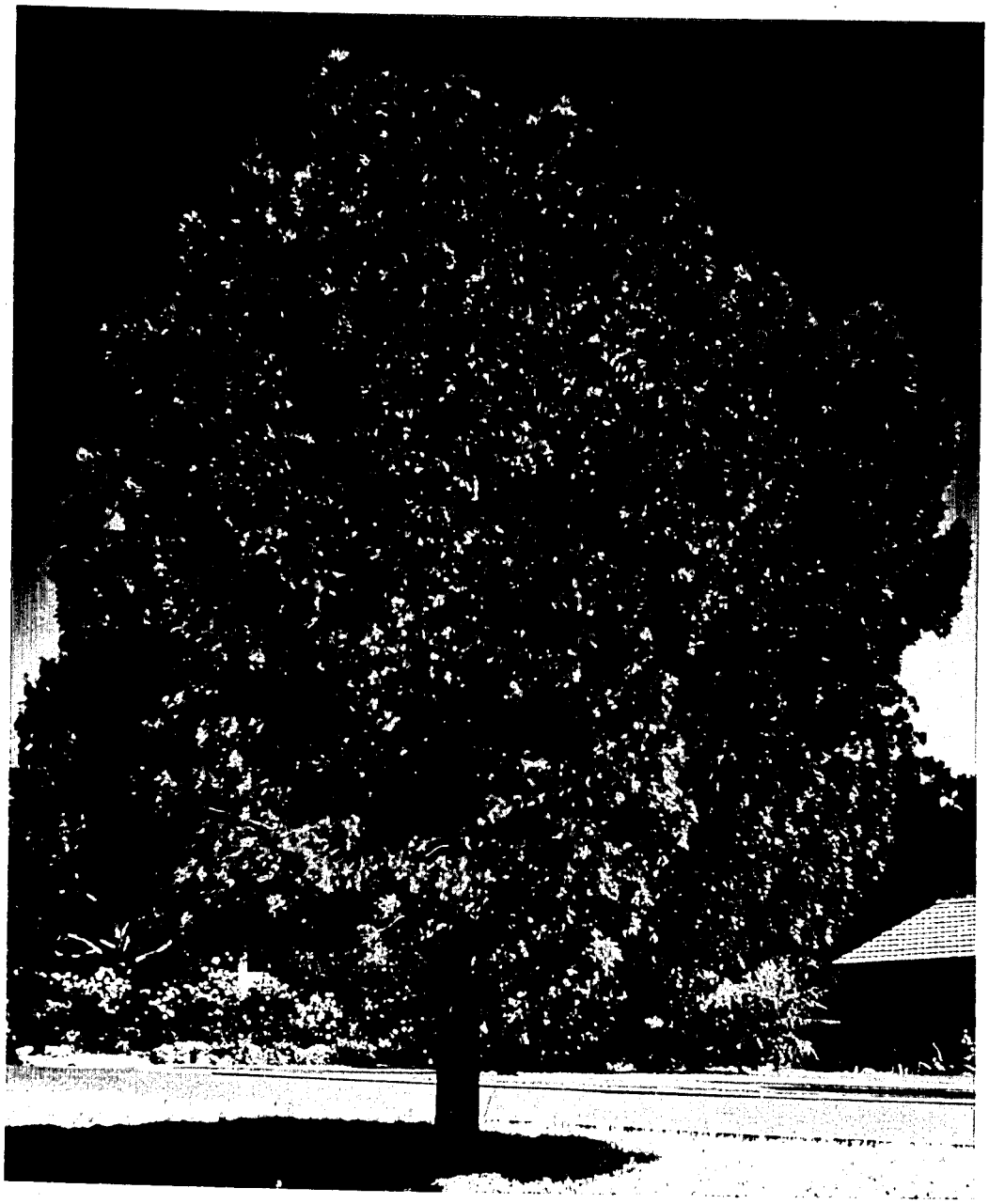
FIG. 1 shows the parent tree in fall coloration.
Figure 2:
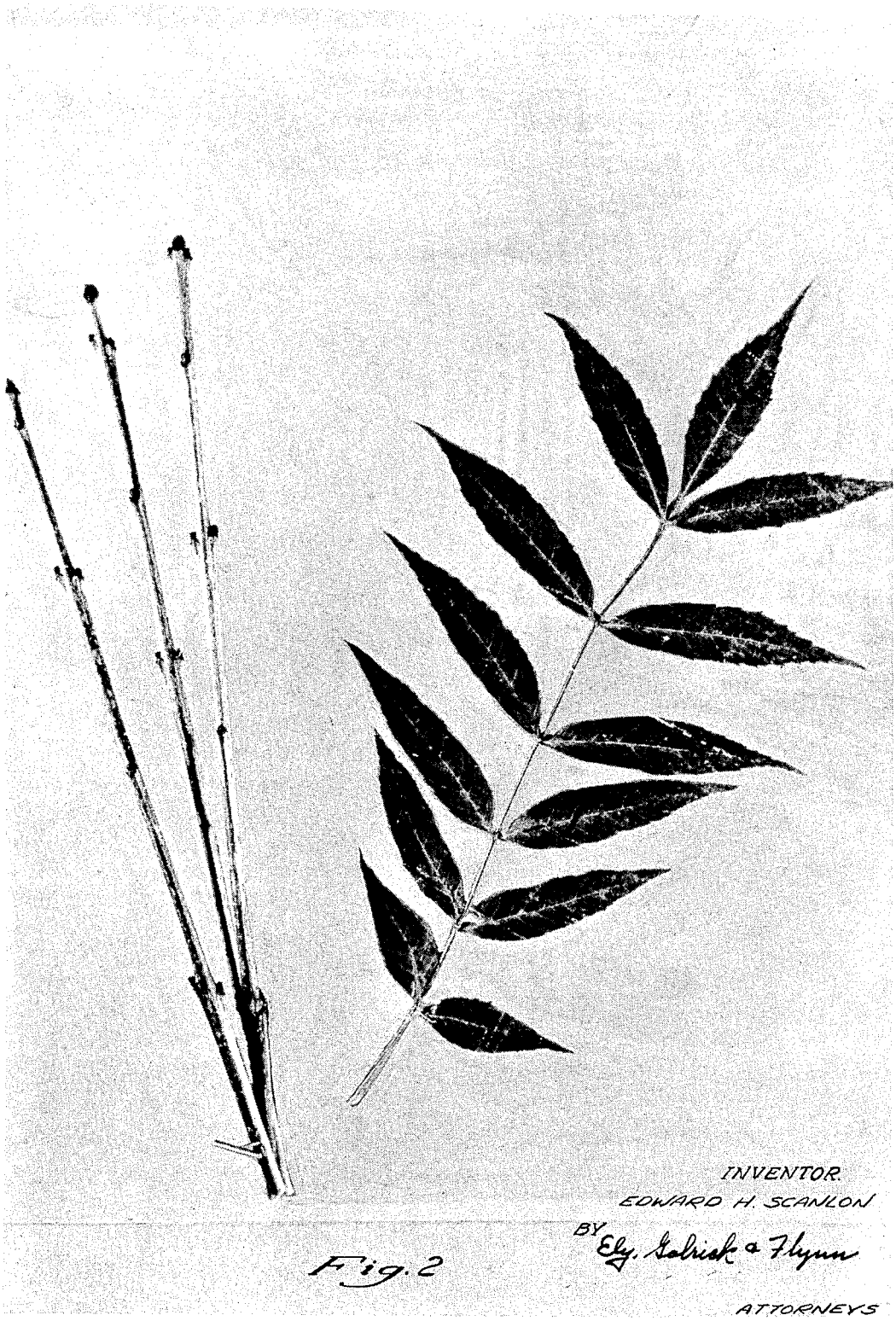
FIG. 2 shows a leaf and twigs of the new variety.

In the drawing of the parent tree is shown the outstanding fall color whereby this new variety is particularly distinguished from the species and other varieties thereof; and also the apparently characteristic tighter, more rounded and symmetrical head form of this variety as compared with the species.

The final autumnal coloration designated by the notation of and determined from the "Nickerson Color Fan, Maximum Chroma, 40 Hues" (published by Munsell Color Co., Inc., Baltimore, Maryland, 1957), is approximately 7.5 Red 3/6 interpolated to 7 Red 4/11; or designated in terms of the Munsell notation (Munsell Book of Color, a Revision and Extension of "The Atlas of the Munsell Color System," by A. H. Munsell, Munsell Color Company, Inc., Baltimore, Maryland, 1929) is predominantly R14/4 (red, chroma 14, value 4) but ranging in value from 2 to 6 inclusive, and in chroma from 4 to 14 inclusive, with traces of RYR10/6 (red yellow red, chroma 10, value 6).

In contract with this new variety, the fall coloration of the species *Fraxinus oxycarpa* is not consistent as to the change from green. Some trees may turn to purple; few to red and some merely brown up and drop. Although this new variety has about the same coloration effect in the fall as *Fraxinus oxycarpa* Raywood, it has the aforementioned additional and very desirable impressive round-headed form contrasted with the more rectangular habit of the Raywood variety observed by applicant.

This new variety has been asexually reproduced by budding and grafting at Portland, Oregon.

I claim:

A new and distinct variety of *Fraxinus oxycarpa* ash tree as illustrated and described, characterized particularly by its autumn coloration.

No references cited.

ABRAHAM G. STONE, *Primary Examiner.*

T. GRAHAM CRAVER, *Examiner.*